United States Patent [19]

Nadolsky et al.

[11] 4,306,032

[45] Dec. 15, 1981

[54] QUATERNIZATION OF AMINES ENTRAINED IN A MICROPOROUS MATRIX

[75] Inventors: Richard J. Nadolsky, Darien; Gwen Dragutinovich, Cicero, both of Ill.

[73] Assignee: Akzona Incorporated, Asheville, N.C.

[21] Appl. No.: 131,308

[22] Filed: Mar. 18, 1980

[51] Int. Cl.³ .............................................. C08J 9/36
[52] U.S. Cl. ........................................ 521/55; 521/53
[58] Field of Search .................................... 521/53, 55

[56] References Cited

U.S. PATENT DOCUMENTS 3,933,697  1/1976  Fuji et al. ............................ 521/55
4,247,498  1/1981  Castro ................................. 264/41

Primary Examiner—Morton Foelak
Attorney, Agent, or Firm—Francis W. Young; Robert F. Green

[57] ABSTRACT

An improved process for quaternizing a tertiary amine entrained in a microporous matrix is disclosed. The improvement comprises subjecting the microporous matrix to methyl chloride vapors for a length of time sufficient to distribute methyl chloride throughout the matrix at a temperature at which substantially no quaternization of the amine occurs. Subsequently, the matrix is heated to a temperature, and for a time sufficient to quaternize the amine.

10 Claims, No Drawings

QUATERNIZATION OF AMINES ENTRAINED IN A MICROPOROUS MATRIX

BACKGROUND OF THE INVENTION

This invention relates to a process for quaternizing tertiary amines in a microporous matrix.

It has been known heretofore that tertiary amines may be quaternized with an alkylating agent such as methyl chloride to yield a quaternary ammonium compound. It has also been known that such compounds may be useful in conditioning fabrics, as by rendering them soft or anti-static. U.S. Patent Application filed concurrently with this application, by A. J. Castro entitled "Dryer-Applied Fabric Composition", (Ser. No. 131,307) discloses a method for conditioning damp fabrics in an automatic dryer. The method disclosed therein comprises tumbling the damp fabrics under heat in a clothes dryer and concurrently contacting said clothes with a 3-dimensional microporous matrix containing a fabric-conditioning agent, for a length of time sufficient to transfer an effective amount of conditioning agent to such fabrics.

As quaternary ammonium compounds are useful conditioning agents, it has become desirable to load such quaternary ammonium compounds into the 3-dimensional microporous matrix disclosed in the aforementioned Patent Application by A. J. Castro. However, the loading of such quaternary ammonium compounds directly into such a microporous matrix is, at best, cumbersome. There has therefor arisen a need for an improved process for entraining such quaternary ammonium compounds in the aforementioned microporous matrix.

As the reaction between tertiary amines and alkylating agents, such as methyl chloride, is well known in the art, one possibility for loading such quaternary ammonium compounds into such a microporous matrix would be to simply load the microporous matrix with the tertiary amine, initially, then to quaternize the amine, in situ. Such a process is desirable, as certain tertiary amines may be utilized to directly form a microporous matrix as disclosed in U.S. Patent Application No. 814,351, filed July 11, 1977, entitled "Microporous Polymer Products and Methods for Making Same", by A. J. Castro. However, initial attempts to quaternize such amines in situ proved to be very time consuming and only partially successful. Thus, there arose a need for an improved process for quaternizing such tertiary amines entrained in a 3-dimensional microporous matrix.

SUMMARY OF THE INVENTION

The Applicant has now discovered an improved process for quaternizing a tertiary amine entrained in a microporous matrix, the improvement comprising subjecting the microporous matrix to methyl chloride vapors for a length of time sufficient to distribute methyl chloride substantially uniformly throughout the matrix, at a temperature at which substantially no quaternization of the amine entrained in the microporous matrix occurs. Subsequently, the microporous matrix containing the tertiary amine and the methyl chloride is heated to a temperature and for a time sufficient to quaternize at least a portion of the amine.

DETAILED DESCRIPTION OF THE PREFERRED EMBODIMENTS

Microporous Matrix

In the practice of the present invention, any 3-dimensional microporous matrix may be utilized. Preferably, in the 3-dimensional microporous matrix the average pore size as measured by mercury intrusion porosimetry, should be within the range of about 0.2 microns to about 40 microns. More preferably, the microporous matrix has an average pore size within the range from about 5 to about 20 microns and most preferably, within the range from about 10 to about 20 microns.

The preferred microporous matrix for use in the practice of the present invention is made in accordance with the teachings of the aforesaid U.S. Patent Application No. 814,351. The aforementioned U.S. Patent Application corresponds to Belgian Pat. No. 858,245, issued Feb. 28, 1978.

For a full understanding of the techniques for preparing the preferred microporous matrix, one may refer to the entire specification of said U.S. Patent Application No. 814,351 which is incorporated herein by reference. Briefly, however, the method comprises heating the desired resin with a compatible liquid to a temperature sufficient to form a homogeneous solution. The solution is allowed to assume the desired shape and cooled at a rate such that liquid-liquid phase separation occurs under non-equilibrium thermodynamic conditions. In the most preferred embodiment, the rate of cooling is such that the compatible liquid forms a plurality of liquid droplets of substantially the same size in a continuous liquid polymer phase. Subsequently, the cooling is continued to solidify the polymer and the compatible liquid is then removed from the resin, resulting in a microporous polymer structure.

The most desired microporous matrix for use in the practice of the present invention is a relatively homogeneous, three-dimensional microporous cellular polymer structure comprising a plurality of substantially spherical cells having an average diameter from about 0.5 to about 100 microns, distributed substantially uniformly throughout the structure, adjacent cells being interconnected by pores smaller in diameter than said microcells, the ratio of the average cell diameter to the average pore diameter being from about 2:1 to about 200:1. Also, preferably, the polymer is a synthetic thermoplastic polymer selected from the group consisting of olefinic polymers, condensation polymers, oxidation polymers, and blends thereof. Said synthetic thermoplastic polymers should be substantially nondeformable at temperatures below about 90° C.

Tertiary Amine

The tertiary amine which is useful in the practice of the present invention is not critical. Any tertiary amine which is "normally liquid" may be utilized. The term "normally liquid" means liquid over the temperature range from about 20° C. to about 100° C. Also, the tertiary amine should not be a solvent for the microporous matrix over the temperature range from about 20° C. to about 100° C.

Generally, the tertiary amines will correspond to the formula:

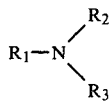

wherein $R_1$ is selected from the group consisting of saturated or unsaturated, straight or branched chain, aliphatic groups, containing from about 8 to about 22 carbon atoms, preferably from about 12 to about 18 carbon atoms, $R_2$ is selected from the group consisting of saturated or unsaturated, straight or branched chain, aliphatic groups containing from about 8 to about 22 carbon atoms, preferably from about 12 to about 18 carbon atoms, short-chain alkyl groups containing from about 1 to about 4 carbon atoms, hydroxyethyl, hydroxypropyl, $(CH_2CH_2O)_g$ $CH_2CH_2OH$, and $(C_3H_6O)_g$ $C_3H_6OH$, wherein g is an integer from 0 to 5, and $R_3$ is selected from the group consisting of short-chain alkyl groups containing from about 1 to about 4 carbon atoms, hydroxyethyl, hydroxypropyl, $(CH_2CH_2O)_h$ $CH_2CH_2OH$ and $(C_3H_6O)_h$ $C_3H_6OH$, wherein h is an integer from 0 to 5.

From the foregoing it is quite apparent that it is impossible to explicitly indicate every possible tertiary amine compound which may be utilized in the practice of the instant invention. However, by referring to the foregoing parameters, one skilled in the art may readily select an appropriate tertiary amine compound for use in performing the instant process.

It should be noted that in many instances the tertiary amine may contain some impurities such as primary and secondary amine as well as tri(long-chain) aliphatic amine.

The amine may in some instances be capable of acting as a compatible liquid when the microporous matrix is in accordance with U.S. Patent Application No. 814,351. If such is the case, it is most advantageous to utilize the tertiary amine to form the microporous matrix initially, thus eliminating the necessity for forming the microporous structure with another compatible liquid, removing the same, and replacing the compatible liquid with the tertiary amine. Thus, if the tertiary amine to be incorporated in the microporous matrix is, for example, N,N-bis(2-hydroxyethyl) tallow amine, the same may be heated with, for example, polypropylene to form a homogeneous solution which is subsequently cooled as discussed hereinabove, resulting in the formation of the microporous matrix containing the N,N,-bis(2-hydroxyethyl) tallow amine. Such a microporous matrix containing the aforementioned amine may then be used directly in the practice of the process of the present invention.

In other instances, however, the tertiary amine to be utilized in the microporous matrix may not be capable of performing as a compatible liquid so that it cannot be directly entrained in such a microporous matrix. In such an instance, it is possible to first form a microporous matrix utilizing a different material as the compatible liquid in the process for initially forming the microporous matrix, and subsequently removing such a compatible liquid to leave behind a void microporous structure. The void structure may then be reloaded with the desired tertiary amine. Such reloading may be accomplished by simply immersing the void microporous matrix in the tertiary amine to be loaded therein. Alternatively, the compatible liquid initially utilized may be pressure displaced by the desired tertiary amine.

Process Conditions

As previously indicated, initial attempts to form the in situ quaternized material were very time consuming and less than totally successful. In such attempts, the microporous matrix containing the tertiary amine was exposed to methyl chloride under quaternization conditions, but without the formation of the desired amount of quaternary ammonium compound, after rather lengthy reaction times. The Applicant then discovered the successfully produced in situ quaternary ammonium compounds could only be made if the microporous matrix containing the amine to be quaternized was first "marinated" in the alkylating agent, such as methyl chloride. The desired microporous matrix containing the tertiary amine to be quaternized typically is marinated in the alklating agent, such as methyl chloride, at a temperature from about 10° to about 30° C., preferably from about 15° to about 25° C., and most preferably from about 18° to about 21° C., to minimize the amount of quaternization that may occur during the marination process. Marination, simply, is the exposure of the microporous matrix to a substantially saturated gaseous environment consisting essentially of methyl chloride vapor.

Such marination may be performed by placing the suitable microporous matrix into an autoclave which is then purged, evacuated, or simply directly attached to a cylinder of methyl chloride. The methyl chloride may then be introduced into the autoclave at a temperature of, for example, about 18° C. at about 52 psig.

The methyl chloride should be introduced into the autoclave in such a manner that no liquid methyl chloride is in contact with the microporous matrix, to prevent dissolution of the tertiary amine into the methyl chloride. The temperature and pressure conditions should simply be such that the aforementioned criteria, no liquid methyl chloride in contact with the microporous matrix, is achieved. Of course, at low marination temperatures the vapor pressure of the methyl chloride will be corresponding low and will require longer marination times. The marination time may typically be less than about 5 hours when a marination temperature of about 20° C. is utilized. Marination times at about 20° C. in excess of 5 hours have not been found to possess any particular advantage over shorter marination times, when the total time for marination and quaternization is viewed as a whole. The length of marination should simply be sufficient to substantially distribute the methyl chloride throughout the microporous matrix.

After the microporous matrix is suitably marinated, the temperature of the matrix may be raised to a temperature sufficient to initiate quaternization. Typically, the temperature may be about 80° C. The microporous matrix is held at such a temperature for a sufficient length of time to quaternize at least a portion of the amine which is initially entrained in the matrix. It may be desirable to quaternize less than 100% of the initially present amine, so that a combination of conditioning effects may be achieved with both the initial tertiary amine and the in situ formed quaternary ammonium compound. After the reaction has proceeded for a sufficient length of time, the methyl chloride is removed or collected. For example, the reaction chamber may be flushed with an inert gas or a vacuum may be applied to remove the residual methyl chloride. Preferably, the methyl chloride is removed while the sample is still at an elevated temperature, although it is possible to remove the methyl chloride during or after cooling of the sample.

Finally, the microporous matrix is allowed to cool to room temperature and if any surface exudation has occurred, it may be optionally removed, physically, or with a solvent wash. A typical exudate would be small amounts of the quaternary ammonium compound. Again, optionally, the resulting microporous matrix may be subsequently trimmed to any desired shape.

COMPARATIVE EXAMPLE

To demonstrate that the degree of quaternization obtained, utilizing a conventional quaternization process without marination, is less than desirable, a three-dimensional microporous matrix having an average pore size of about 7 microns formed from 20% polypropylene and 80% N,N-bis(2-hydroxyethyl) tallow amine, in accordance with the teachings of U.S. Patent Application No. 814,351, still containing the amine was formed in a cylindrical shape having a length of 2.8 cm and a diameter of 1.8 cm, weighing 5.5 grams, with the ends being closed by heat sealing. The cylinder was placed in an autoclave which was then evacuated to approximately 25 inches of mercury. The reactor was then filled with methyl chloride to a pressure of 50 psig at 93° C. After 23½ hours of reaction time an exudate was observed and the pressure had fallen to 32 psig. The methyl chloride was evacuated and the cylinder removed and analyzed to contain 53.3 percent of quaternary, based upon the orginally present amine.

The foregoing Comparative Example demonstrates that utilizing a conventional quaternization technique, without premarination of the matrix, undesirably low conversions and lengthy reaction times are necessary.

A more complete understanding of the scope of the Applicant's invention may be had by referring to the following non-limiting examples. In all the following Examples the standard microporous matrix which was utilized was formed by heating polypropylene (Marlex ®, Phillips Petroleum Company) with N,N-bis(2-hydroxyethyl) tallow amine (Armostat ® 310 Armak Company) to a temperature at which a homogeneous solution is formed, typically about 200° C. 80% by weight of the tertiary amine and 20% by weight, of the polypropylene was utilized. Approximately 1 kilogram of the solution was poured into a glass cake dish which was held at an elevated temperature, typically 180° to 200° C., with a hot plate. The dimensions of the cake dish were approximately 13 inches by 9 inches by 2 inches. The cake dish was removed from the hot plate as soon as any air bubbles which formed, if any, had escaped from the solution.

The solution in the cake dish was allowed to cool and the resulting solid was removed therefrom. The solid was cut with a table saw to a length of about 7.2 inches and a width of about 3.1 inches and then lathed cut to a suitable thickness. The thus formed panels contained the tertiary amine, N,N-bis(2-hydroxyethyl) tallow amine. The three-dimensional microporous matrix in which the amine was entrained had an average pore size of about 7 microns.

Also, in the following Example, a 2 liter autoclave was utilized which had all extraneous cooling and stirring apparatus removed therefrom. The panels were supported in the autoclave in a manner such that they did not touch any of the walls of the autoclave. Furthermore, in the procedure utilized, the autoclave was first sealed and then purged with nitrogen. Subsequently, the autoclave was evacuated and cooled to the desired temperature. Then, the reactor was charged with methyl chloride to a pressure of about 52 psig (unless otherwise indicated), the maximum pressure at a temperature of about 18° C. After the microporous matrix was suitably marinated, the temperature of the autoclave was raised to about 80° C. over a period of about ½ hour. At a temperature of about 80° C., the pressure in the autoclave rose to about 100 psig. After a suitable quaternization time, the reactor was subsequently vented and evaporated to about 25 millimeters mercury, to remove any excess methyl chloride. Finally, the autoclave was opened and the samples removed.

EXAMPLES 1-4

To determine the effect of the marination time on the ultimate yield of quaternary ammonium compound, the standard microporous matrix as described hereinabove containing N,N-bis(2-hydroxyethyl) tallow amine was marinated at 18° C. and 52 psig methyl chloride pressure, for times of 0.5 hours (Example 1), 1.0 hours (Example 2), 3.0 hours (Example 3), and 5.0 hours (Example 4). Subsequently, the samples were quaternized for 17 hours at approximately 80° C. The results of the foregoing examples are summarized in Table I.

TABLE I

| Example Number | Percent Conversion |
|---|---|
| 1 | 90.86 |
| 2 | 93.13 |
| 3 | 94.88 |
| 4 | 97.88 |

The results shown in Table I demonstrate that with an increase in marination time, a corresponding increase in the percentage conversion of tertiary amine to quaternary ammonium compound results.

EXAMPLES 5-9

To determine the effect of the quaternization time on the yield of quaternary ammonium compound, the standard microporous matrix was marinated for 0.5 hours at 18° C. and 52 psig methyl chloride pressure and subsequently quaternized at approximately 80° C. for times of 1.0 hour (Example 5), 2.0 hours (Example 6), 4.0 hours (Example 7), 5.0 hours (Example 8), and 17.0 hours (Example 9). The results are summarized in Table II below:

TABLE II

| Example Number | Percent Conversion |
|---|---|
| 5 | 59.63 |
| 6 | 66.00 |
| 7 | 68.25 |
| 8 | 76.25 |
| 9 | 90.86 |

From the foregoing Table it is apparent that with a marination time of only ½ hour at 18° C., a large increase in the conversion results by increasing the quaternization time from 1 to 17 hours.

EXAMPLES 10-13

To determine the importance of marination time versus quaternization time when the total reaction time is held constant, the standard microporous matrix was marinated at 18° C. and 52 psig methyl chloride pressure and subsequently quaternized at approximately 80° C. The marination times were varied from 0.5 to 4.5 hours and the quaternization time from 5.0 to 1.0 hours. The results are contained in Table III below.

TABLE III

| Example Number | Marination Time in Hours | Quaternization Time in Hours | Percent Conversion |
| --- | --- | --- | --- |
| 10 | 0.5 | 5.0 | 76.25 |
| 11 | 2.0 | 3.5 | 89.75 |
| 12 | 3.5 | 2.0 | 94.13 |
| 13 | 4.5 | 1.0 | 97.00 |

From the foregoing Table III it is apparent that by increasing the marination time up to 4.5 hours, from 0.5 hours, the quaternization time may be reduced to as little as 1.0 hours and still obtain a yield of 97.00%, which is the optimum for the marination time and quaternization time evaluated.

EXAMPLES 14-17

To determine the effect of the temperature of marination on the yield, the standard microporous matrix was marinated at 3° C. and 25 psig methyl chloride pressure. The microporous matrix was subsequently quaternized for 17 hours at approximately 80° C. The marination times utilized were 0.5 hour (Example 14), 1.0 hour (Example 15), 3.0 hours (Examples 16), and 5.0 hours (Example 17). The results are summarized in Table IV below.

TABLE IV

| Example Number | Percent Conversion |
| --- | --- |
| 14 | 43.88 |
| 15 | 55.25 |
| 16 | 62.88 |
| 17 | 59.13 |

From the foregoing results in Table IV it is apparent that at 3° C. a lower limit of the useful marination temperature has apparently been reached for the particular microporous resin matrix utilized as even long marination time of 3.0 and 5.0 hours coupled with seventeen hour quaternization times yielded only approximately 60% conversion of the tertiary amine into the desired quaternary ammonium compound, as compared to marination times of, for example, 5.0 hours at 18° C., and quaternization times of 1 hour yielding a percent conversion of 97.88.

All of the foregoing Examples demonstrate the fact that by marinating the microporous matrix prior to performing quaternization of the tertiary amine, not only may be the tertiary amine quaternize in situ, but by appropriately considering the combined effects of marination and quaternization times, one may effectively optimize the total of both to obtain a substantially reduced overall marination and quaternization reaction time.

What is claimed is:

1. An improved process for quaternizing a normally liquid tertiary amine entrained in a three-dimensional synthetic thermoplastic polymeric microporous matrix having an average pore size from about 0.2 to about 40 microns wherein the improvement comprises subjecting the microporous matrix to methyl chloride vapors for a length of time sufficient to distribute methyl chloride throughout the matrix, at a temperature at which substantially no quaternization of the amine occurs and subsequently heating the matrix to a temperature and for a time sufficient to quaternize at least a portion of the amine.

2. The process of claim 1 wherein the matrix has an average pore size from about 5 to about 20 microns.

3. The process of claim 1 wherein the matrix has an average pore size from about 10 to about 20 microns.

4. The process of claim 1 wherein the matrix is a relatively homogeneous cellular polymer structure comprising a plurality of substantially spherical cells having an average diameter from about 0.5 to about 100 microns, distributed substantially uniformly throughout the structure, adjacent cells being interconnected by pores smaller in diameter than said cells, the ratio of the average cell diameter to the average pore diameter being from about 2:1 to about 200:1.

5. The process of claim 1 or 4 wherein the microporous matrix is comprised of a synthetic thermoplastic polymer selected from the group consisting of olefinic polymers, condensation polymers, oxidation polymers, and blends thereof.

6. The process of claim 5 wherein the thermoplastic polymer is substantially nondeformable at temperatures below about 90° C.

7. The process of claim 1 wherein the tertiary amine has the formula

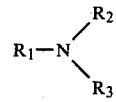

wherein $R_1$ is selected from the group consisting of aliphatic groups, containing from about 8 to about 22 carbon atoms. $R_2$ is selected from the group consisting of aliphatic groups containing from about 8 to about 22 carbon atoms, short-chain alkyl groups containing from about 1 to about 4 carbon atoms, hydroxyethyl, hydroxypropyl, $(CH_2CH_2O)_g$ $CH_2CH_2OH$, and $(C_3H_6O)_g$ $C_3H_6OH$, wherein g is an integer from 0 to 5, and $R_3$ is selected from the group consisting of short-chain alkyl groups containing from about 1 to about 4 carbon atoms, hydroxyethyl, hydroxypropyl, $(CH_2CH_2O)_h$ $CH_2CH_2OH$ and $(C_3H_6O)_h$ $C_3H_6OH$, wherein h is an integer from 0 to 5.

8. The process of claim 1 or 7 wherein the microporous matrix is subjected to methyl chloride vapors at a temperature from about 10° to about 30° C.

9. The process of claim 8 wherein the microporous matrix is subjected to methyl chloride vapors at a temperature from about 15° to about 25° C.

10. The process of claim 8 wherein the microporous matrix is subjected to methyl chloride vapors at a temperature from about 18° to about 21° C.

* * * * *